United States Patent
Clary et al.

(10) Patent No.: US 7,285,568 B2
(45) Date of Patent: Oct. 23, 2007

(54) BIAROMATIC COMPOUNDS WHICH ACTIVATE PPARGAMMA TYPE RECEPTORS AND COSMETIC/PHARMACEUTICAL COMPOSITIONS COMPRISED THEREOF

(75) Inventors: Laurence Clary, La Colle sur Loup (FR); Claire Bouix-Peter, Le Cannet (FR); Michel Rivier, Nice (FR); Pascal Collette, Le Cannet (FR); Andre Jomard, Saint Vallier de Thiey (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 11/135,499

(22) Filed: May 24, 2005

(65) Prior Publication Data
US 2006/0004048 A1    Jan. 5, 2006

Related U.S. Application Data (63) Continuation of application No. PCT/EP2003/015002, filed on Nov. 21, 2003.

(60) Provisional application No. 60/430,698, filed on Dec. 4, 2002.

(30) Foreign Application Priority Data
Nov. 25, 2002   (FR)   .................... 02 14793

(51) Int. Cl.
*A61K 31/42*   (2006.01)
*A61K 31/5377*   (2006.01)
*C07D 261/02*   (2006.01)
*C07D 265/30*   (2006.01)

(52) U.S. Cl. ................. 514/378; 514/231.2; 514/364; 514/317; 544/98; 546/226; 546/207; 548/240; 548/215; 564/50

(58) Field of Classification Search ........... 564/50; 546/192, 226, 207; 514/317, 364, 362, 363; 548/215, 146, 206
See application file for complete search history.

(56) References Cited

U.S. PATENT DOCUMENTS

| 6,908,939 B2 * | 6/2005 | Bernardon et al. ......... 514/369 |
| 2006/0148862 A1 * | 7/2006 | Clary et al. ................ 514/362 |

\* cited by examiner

*Primary Examiner*—Rebecca Anderson
*Assistant Examiner*—Yong Chu
(74) *Attorney, Agent, or Firm*—Buchanan, Ingersoll & Rooney, PC (57) ABSTRACT

Novel biaromatic compounds having the structural formula (I) below:

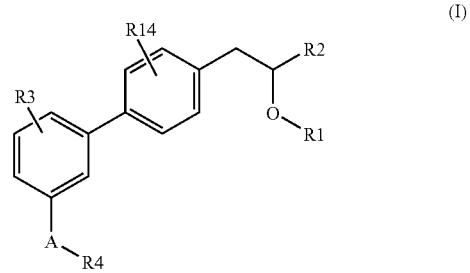

are formulated into pharmaceutical compositions suited for administration in human or veterinary medicine (in dermatology, and also in the fields of cardiovascular diseases, immune diseases and/or diseases associated with lipid metabolism), or, alternatively, into cosmetic compositions.

Figure 1:
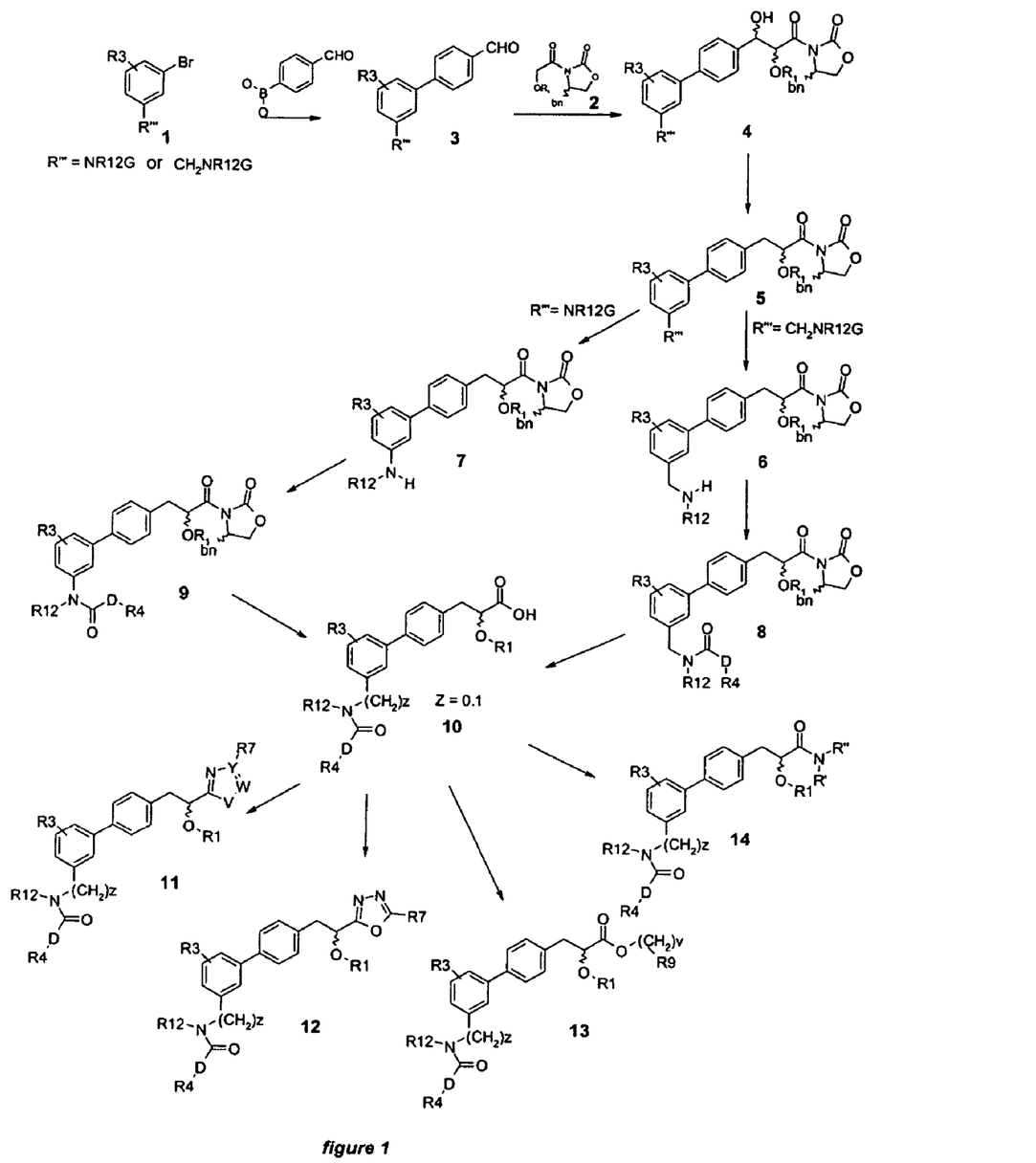

14 Claims, 3 Drawing Sheets figure 1

Figure 3:
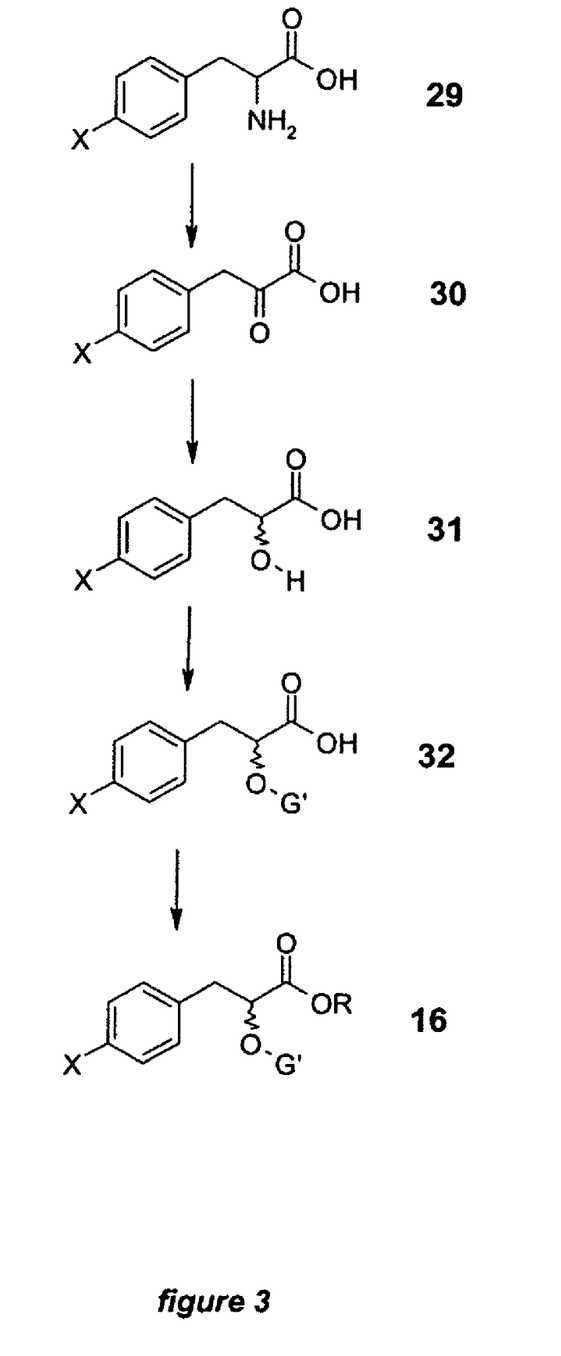

Figure 2 figure 3

US 7,285,568 B2

BIAROMATIC COMPOUNDS WHICH ACTIVATE PPARGAMMA TYPE RECEPTORS AND COSMETIC/PHARMACEUTICAL COMPOSITIONS COMPRISED THEREOF

CROSS-REFERENCE TO PRIORITY/PCT/PROVISIONAL APPLICATIONS

This application claims priority under 35 U.S.C. § 119 of FR 02/14793, filed Nov. 25, 2002, and of provisional application Ser. No. 60/430,698, filed Dec. 4, 2002, and is a continuation of PCT/EP 2003/015002, filed Nov. 21, 2003 and designating the United States (published in the English language on Jun. 10, 2004 as WO 2004/048351 A3); each hereby expressly incorporated by reference and each assigned to the assignee hereof.

BACKGROUND OF THE INVENTION

1. Technical Field of the Invention

The present invention relates to a novel class of biaromatic compounds which are modulators of receptors of Peroxisome Proliferator-Activated Receptor type of subtype γ (PPAR-γ). This invention also relates to a process for the preparation thereof and to their formulation into pharmaceutical compositions suited for human or veterinary medicine, or alternatively for cosmetic compositions.

2. Description of Background and/or Related and/or Prior Art

The activity of receptors of PPAR type has been the subject of many studies. Mention may be made, as a guide, of the publication entitled "Differential Expression of Peroxisome Proliferator-Activated Receptor Subtypes During the Differentiation of Human Keratinocytes", Michel Rivier et al., *J. Invest. Dermatol*, 111, 1998, pp. 1116-1121, in which are listed a large number of bibliographic references relating to receptors of PPAR type. Mention may also be made, as a guide, of the report entitled "The PPARs: From orphan receptors to Drug Discovery", Timothy M. Willson, Peter J. Brown, Daniel D. Sternbach and Brad R. Henke, *J. Med. Chem.*, 2000, Vol. 43, pp. 527-550.

PPAR receptors activate transcription by binding to elements of DNA sequences, known as peroxisome proliferator response elements (PPRE), in the form of a heterodimer with retinoid X receptors (known as RXRs).

Three subtypes of human PPAR have been identified and described: PPARα, PPARγ and PPARδ (or NUC1).

PPARα is mainly expressed in the liver, while PPARδ is ubiquitous.

PPARγ is the most extensively studied of the three subtypes. All prior art references suggest a critical role of PPARγ in regulating the differentiation of adipocytes, where it is greatly expressed. It also has a key role in systemic lipid homeostasis.

It has been described, in particular in WO 96/33724, that PPARγ-selective compounds, such as a prostaglandin-J2 or -D2, are potential active agents for treating obesity and diabetes.

Moreover, the assignee hereof has already described PPARγ compounds and/or the use thereof in the following patent applications. FR 98/02894 describes the use of PPARγ activator compounds in the preparation of a pharmaceutical composition, the composition being intended to treat skin disorders associated with an anomaly of epidermal cell differentiation. WO 01/02543 describes a novel class of PPARγ-modulating compounds.

SUMMARY OF THE INVENTION

A novel class of PPARγ-modulating compounds has now been developed that exhibit very good specific affinity for PPARγ.

Thus, the present invention features novel compounds having the general formula (I) below:

(I)

in which $R_1$ is an alkyl radical having from 1 to 12 carbon atoms, or a radical selected from among those of formulae a)-c):

a)

b) —$(CH_2)_m$—$(CO)_n$—$(X)_p$—$(CH_2)_q$—$R_5$ or
c) α-amino acid N-protected with standard amine-protecting groups, such as 9-fluorenylmethylcarbamate (FMOC), t-butylcarbamate (BOC), benzyl or trifluoroacetyl, wherein $R_5$, X, m, n, p and q are as defined below;

$R_2$ is a radical selected from among those of formulae (a)-(c):

(a)

(b)

(c)

wherein $R_7$, $R_8$, V, W and Y are as defined below; $R_3$ is a hydrogen atom, a halogen atom, an alkyl radical having from 1 to 12 carbon atoms, a hydroxyl radical, an alkoxy radical having from 1 to 7 carbon atoms, an aralkoxy radical, an aryloxy radical, a polyether radical, a nitro radical, or an amino radical optionally substituted with one or more alkyl radicals having from 1 to 12 carbon atoms, an aryl radical, an aralkyl radical, a heteroaryl radical or a heterocyclic radical; $R_4$ is an alkyl radical having from 1 to 12 carbon atoms, an aryl radical, an aralkyl radical, a heteroaryl radical, a heterocyclic radical or a 9-fluorenylmethyl radical, a radical —(CH$_2$)$_a$—(N—R$_{12}$)$_b$—(CO)$_c$—R$_6$ or a radical, —(CH$_2$)$_a$—(N—R$_{12}$)$_b$—(CNR$_{15}$)$_c$—R$_6$, wherein R$_6$, R$_{12}$, R$_{15}$, a, b and c are as defined below; R$_5$ is a hydrogen atom, an alkyl radical having from 1 to 12 carbon atoms, an alkoxy radical having from 1 to 7 carbon atoms, an aralkoxy radical, an aryloxy radical, an aryl radical, an aralkyl radical, a heteroaryl radical, a heterocyclic radical or a group (CO)$_s$(Z)$_t$R$_6$, wherein Z, R$_6$, s and t are as defined below; a, b, c, m, n, p, q, s and t have the values 0, 1 or 2; X is an oxygen or sulfur atom or NR$_6$, wherein R$_6$ is as defined below; V is an oxygen, nitrogen or sulfur atom; W is a nitrogen atom or a radical C—R$_{10}$, wherein R$_{10}$ is as defined below; Y is a nitrogen atom or a carbon atom; Z is an oxygen, nitrogen or sulfur atom; R$_6$ and R$_7$, which may be identical or different, are each a hydrogen atom, an alkyl radical having from 1 to 12 carbon atoms, an aryl radical, an aralkyl radical, a heteroaryl radical or a heterocyclic radical; R$_{15}$ is a hydrogen atom, an alkyl radical having from 1 to 12 carbon atoms, an aryl radical, an aralkyl radical, a heteroaryl radical or a heterocyclic radical; R$_8$ is a radical O—(CH$_2$)$_v$—R$_9$, a hydroxyl radical, an alkoxy radical having from 1 to 7 carbon atoms, an aralkoxy radical, an aryloxy radical, an aryl radical, an aralkyl radical, a heteroaryl radical, a heterocyclic radical, or the radical:

wherein R$_9$, R' and R" are as defined below, with the proviso that when R$_1$ is an alkyl radical having from 1 to 12 carbon atoms, a radical of formula a), a radical of formula b) being an alkyl radical having from 1 to 12 carbon atoms, an aryl or aralkyl radical, then R$_8$ is not a hydroxyl radical or alkoxy radical having from 1 to 7 carbon atoms; R' is a heteroaryl radical or a heterocyclic radical; R" is a hydrogen atom, an alkyl radical having from 1 to 12 carbon atoms, an aryl radical, an aralkyl radical, optionally substituted with one or more halogen atoms, a heteroaryl radical, a heterocyclic radical or a radical (CH$_2$)$_v$—R$_9$, wherein R$_9$ and v are as defined below; R$_9$ is an aryl, aralkyl or heteroaryl radical, a heterocyclic radical, a radical NH—CO—R$_{10}$, a radical NH—CO—O—R$_{10}$ or C—R$_{10}$R$_{11}$ or a radical NR$_{10}$R$_{11}$, wherein R$_{10}$ and R$_{11}$ are as defined below; v has the values 1, 2 or 3; R$_{10}$ is a hydrogen atom, an alkyl radical having from 1 to 12 carbon atoms, an aryl radical, an aralkyl radical, a heteroaryl radical or a heterocyclic radical; R$_{11}$ is a hydrogen atom or an alkyl radical having from 1 to 3 carbon atoms; R$_{14}$ is a halogen atom; A is a radical having the following structure: —(CH$_2$)$_z$—(N—R$_{12}$)$_y$—(CO)$_x$—(D)$_w$ or —(CH$_2$)$_z$—(N—R$_{12}$)$_y$—(CS)$_x$—(D)$_w$, wherein D, w, x, y, z and R$_{12}$ are as defined below; D is an oxygen or sulfur atom, a radical —NR$_{13}$ or a CH$_2$ radical; R$_{13}$ is as defined below; w, x, y and z, which may be identical or different, have the values 0 or 1, with the proviso that the sum x+y+z+w is greater than 2, and when x=0, then y or w=0; R$_{12}$ and R$_{13}$ are each a hydrogen atom or an alkyl radical having from 1 to 12 carbon atoms, and the optical and geometrical isomers and salts and mixtures thereof.

DETAILED DESCRIPTION OF BEST MODE AND SPECIFIC/PREFERRED EMBODIMENTS OF THE INVENTION

The present invention also features optical isomers and mixtures of the compounds (I), including racemic mixtures, and mixtures of geometric isomers.

In particular, when the compounds according to the invention are in the form of salts, they are salts of an alkali metal or alkaline-earth metal, zinc salts or salts of an organic amine.

According to the present invention, the term "hydroxyl radical" means an —OH radical.

According to the present invention, the expression "alkyl radical having from 1 to 3 carbon atoms" means a methyl, ethyl or propyl radical.

According to the present invention, the expression "alkyl radical having from 1 to 12 carbon atoms" means a linear or cyclic, optionally branched, hydrogen-containing or fluorine-containing radical having 1 to 12 carbon atoms, which may be interrupted with a hetero atom, and the alkyl radicals having from 1 to 12 carbon atoms are preferably methyl, ethyl, isopropyl, butyl, tert-butyl, hexyl, octyl, decyl or cyclohexyl radicals.

The term "polyether radical" means a polyether radical having from 1 to 6 carbon atoms interrupted with at least one oxygen atom, such as methoxymethoxy, ethoxymethoxy or methoxyethoxymethoxy radicals.

The term "halogen atom" means a fluorine, chlorine or bromine atom.

The term "alkoxy radical having from 1 to 7 carbon atoms" means a radical having from one to seven carbon atoms, such as methoxy, ethoxy, isopropyloxy, tert-butoxy, hexyloxy, which may optionally be substituted with an alkyl radical having from 1 to 12 carbon atoms.

The term "aralkoxy" means in particular benzyloxy.

The term "aryloxy" means in particular phenoxy.

The term "aryl radical" means a phenyl, biphenyl, cinnamyl or naphthyl radical, which may be mono- or disubstituted with a halogen atom, a CF$_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

The term "aralkyl radical" means a benzyl, phenethyl or 2-naphthylmethyl radical, which may be mono- or disubstituted with a halogen atom, a CF$_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

The term "heteroaryl radical" means an aryl radical interrupted with one or more hetero atoms, such as a pyridyl, furyl, thienyl, isoxazolyl, oxadiazolyl, oxazolyl, isothiazolyl, quinazolinyl, benzothiadiazolyl, benzimidazolyl, indolyl or benzofuryl radical, optionally substituted with at least one halogen, an alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

The term "heterocyclic radical" preferably means a morpholino, piperidino, piperazino, 2-oxo-1-piperidyl or 2-oxo-1-pyrrolidinyl radical, optionally substituted with at least one alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

Among the compounds of formula (I) within the scope of the present invention, mention may be made especially of the following compounds (alone or as a mixture):

1. N-{4'-[2-ethoxy-2-(5-propyl[1,3,4]oxadiazol-2-yl)ethyl]biphenyl-3-ylmethyl}-N-methyl-6-(2-methoxyethoxymethoxy)naphthalene-2-carboxylamide;
2. N-{4'-[2-ethoxy-2-(5-propyl[1,3,4]oxadiazol-2-yl)ethyl]biphenyl-3-ylmethyl}-N-methyl-4-phenoxybenzamide;
3. N-{4'-[2-ethoxy-2-(5-propyl[1,3,4]oxadiazol-2-yl)ethyl]biphenyl-3-ylmethyl}-N-methyloctane-1-carboxylamide;
4. N-{4'-[2-ethoxy-2-(5-propyl[1,3,4]oxadiazol-2-yl)ethyl]biphenyl-3-ylmethyl}-N-methylbiphenyl-4-carboxylamide;
5. N-{4'-[2-ethoxy-2-(5-propyl[1,3,4]oxadiazol-2-yl)ethyl]biphenyl-3-ylmethyl}-N-methyl-6-propoxynaphthalene-2-carboxylamide;
6. N-{4'-[2-ethoxy-2-(5-propyl[1,3,4]oxadiazol-2-yl)ethyl]biphenyl-3-ylmethyl}-N-methyl-4'-(2-methoxyethoxymethoxymethyl)biphenyl-4-carboxylamide;
7. methyl 6-({4'-[2-ethoxy-2-(5-propyl[1,3,4]oxadiazol-2-yl)ethyl]biphenyl-3-ylmethyl}methylcarbamoyl)naphthalene-2-carboxylate;
8. 1-[4'-(2-ethoxy-3-morpholin-4-yl-3-oxopropyl)biphenyl-3-yl]-3-heptyl-1-methylurea;
9. 1-{4'-[2-ethoxy-3-(4-methylpiperid-1-yl)-3-oxopropyl]biphenyl-3-yl}-3-heptyl-1-methylurea;
10. 1-{4'-[2-ethoxy-2-(5-propyl[1,3,4]oxadiazol-2-yl)ethyl]biphenyl-3-yl}-3-heptyl-1-methylurea;
11. 3-benzo[1,2,5]thiadiazol-4-yl-1-{4'-[2-ethoxy-3-(4-methylpiperid-1-yl)-3-oxopropyl]biphenyl-3-yl}-1-methylurea;
12. 1-{4'-[2-ethoxy-3-(4-methylpiperid-1-yl)-3-oxopropyl]biphenyl-3-yl}-1-methyl-3-thiophen-2-ylurea;
13. ethyl 1-carboxy-2-[3'-(3-heptyl-1-methylureido)biphenyl-4-yl]pentanoate;
14. ethyl 1-carboxy-2-[3'-(3-heptyl-1-methylureido)biphenyl-4-yl]benzoate;
15. 2-benzyloxy-3-[3'-(3-heptyl-1-methylureido)biphenyl-4-yl]propionic acid;
16. 3-[3'-(3-heptyl-1-methylureido)biphenyl-4-yl]-2-(3-phenylpropionyloxy)propionic acid;
17. 2-butoxy-3-[3'-(3-heptyl-1-methylureido)biphenyl-4-yl] propionic acid;
18. ethyl 1-[3'-(3-heptyl-1-methylureido)biphenyl-4-ylmethyl]-2-(4-methylpiperid-1-yl)-2-oxoisonicotinate;
19. 1-{4'-[2-ethoxy-3-(4-methylpiperid-1-yl)-3-oxopropyl]biphenyl-3-yl}-1-methyl-3-(5-methyl-3-phenylisoxazol-4-yl)urea;
20. 2-benzoimidazol-1-yl-N-{4'-[2-ethoxy-3-(4-methylpiperid-1-yl)-3-oxopropyl]biphenyl-3-ylmethyl}-N-methylacetamide;
21. N-{4'-[2-ethoxy-3-(4-methylpiperid-1-yl)-3-oxopropyl]biphenyl-3-ylmethyl}-N-methyl-2-pyrid-4-ylthiazole-4-carboxylamide;
22. N-{4'-[2-ethoxy-3-(4-methylpiperid-1-yl)-3-oxopropyl]biphenyl-3-ylmethyl}-N-methyl-2-pyrid-4-ylthiazole-4-carboxylamide;
23. N-{4'-[2-ethoxy-3-(4-methylpiperid-1-yl)-3-oxopropyl]biphenyl-3-ylmethyl}-N-methyl-6-hydroxynaphthalene-2-carboxylamide;
24. N-[4'-(2-ethoxy-3-morpholin-4-yl-3-oxopropyl)biphenyl-3-ylmethyl]-N-methyl-6-hydroxynaphthalene-2-carboxylamide;
25. N-[4'-(2-ethoxy-3-morpholin-4-yl-3-oxopropyl)biphenyl-3-ylmethyl]-N-methylquinoxaline-6-carboxylamide;
26. 3-[3'-(3-heptyl-1-methylureido)biphenyl-4-yl]-2-phenoxypropionic acid;
27. 3-[3'-(3-heptyl-1-methylureido)biphenyl-4-yl]-2-phenylacetoxypropionic acid;
28. ethyl 1-carboxy-2-3'-(3-heptyl-1-methylureido)biphenyl-4-yl]-2-aminopropionate;
29. N-[4'-(2-ethoxy-3-oxo-3-piperid-1-ylpropyl)biphenyl-3-ylmethyl]-N-methyl-6-(2-methoxyethoxymethoxy)naphthalene-2-carboxylamide;
30. N-{4'-[2-ethoxy-3-(4-methylpiperid-1-yl)-3-oxopropyl]biphenyl-3-ylmethyl}-N-methyl-6-(2-methoxyethoxymethoxy)naphthalene-2-carboxylamide;
31. N-{4'-[2-ethoxy-3-oxo-3-(4-phenylpiperid-1-yl)propyl]biphenyl-3-ylmethyl}-N-methyl-6-(2-methoxyethoxymethoxy)naphthalene-2-carboxylamide;
32. N-{4'-[2-ethoxy-2-(3-methylbutylcarbamoyl)ethyl]biphenyl-3-ylmethyl}-N-methyl-6-(2-methoxyethoxymethoxy)naphthalene-2-carboxylamide;
33. N-{4'-[2-(cyclohexylmethylcarbamoyl)-2-ethoxyethyl]biphenyl-3-ylmethyl}-N-methyl-6-(2-methoxyethoxymethoxy)naphthalene-2-carboxylamide;
34. N-{4'-[2-ethoxy-2-(ethylpyrid-4-ylmethylcarbamoyl)ethyl]biphenyl-3-ylmethyl}-N-methyl-6-(2-methoxyethoxymethoxy)naphthalene-2-carboxylamide;
35. N-(4'-{2-[(2-dimethylaminoethyl)ethylcarbamoyl]-2-ethoxyethyl}biphenyl-3-ylmethyl)-N-methyl-6-(2-methoxyethoxymethoxy)naphthalene-2-carboxylamide;
36. N-{4'-[2-ethoxy-2-(2-piperid-1-ylethylcarbamoyl)ethyl]biphenyl-3-ylmethyl}-N-methyl-6-(2-methoxyethoxymethoxy)naphthalene-2-carboxylamide;
37. N-[4'-(2-ethoxy-3-morpholin-4-yl-3-oxopropyl)biphenyl-3-ylmethyl]-N-methyl-6-(2-methoxyethoxymethoxy)naphthalene-2-carboxylamide;
38. N-{4'-[2-(benzylmethylcarbamoyl)-2-ethoxyethyl]biphenyl-3-ylmethyl}-N-methyl-6-(2-methoxyethoxymethoxy)naphthalene-2-carboxylamide;
39. N-{4'-[2-ethoxy-3-(4-methylpiperazin-1-yl)-3-oxopropyl]biphenyl-3-ylmethyl}-N-methyl-6-(2-methoxyethoxymethoxy)naphthalene-2-carboxylamide;
40. N-{4'-[2-(cyclohexylmethylcarbamoyl)-2-ethoxyethyl]biphenyl-3-ylmethyl}-N-methyl-6-(2-methoxyethoxymethoxy)naphthalene-2-carboxylamide;
41. 1-{4'-[2-cyclopropylmethoxy-3-(4-methylpiperid-1-yl)-3-oxopropyl]biphenyl-3-yl}-3-hexyl-1-methylthiourea;
42. 1-{4'-[2-ethoxy-3-(4-methylpiperid-1-yl)-3-oxopropyl]biphenyl-3-yl}-3-hexyl-1-methylthiourea;
43. 1-[4'-(2-ethoxy-3-morpholin-4-yl-3-oxopropyl)biphenyl-3-yl]-3-hexyl-1-methylthiourea;
44. [4'-(2-ethoxy-3-morpholin-4-yl-3-oxopropyl)4-fluorobiphenyl-3-ylmethyl]methyloctanoylamide;
45. 4'-(2-ethoxy-3-morpholin-4-yl-3-oxopropyl)-6-fluorobiphenyl-3-ylmethyl]methyloctanoylamide;
46. 1-[4'-(2-ethoxy-3-morpholin-4-yl-3-oxopropyl)-6-fluorobiphenyl-3-yl]-3-heptyl-1-methylurea;
47. 1-{4'-[2-ethoxy-3-(4-methylpiperid-1-yl)-3-oxopropyl]-6-fluorobiphenyl-3-yl}-3-heptyl-1-methylurea;

48. 1-{4'-[2-ethoxy-3-(4-methylpiperid-1-yl)-3-oxopropyl]-4-fluorobiphenyl-3-yl}-3-heptyl-1-methylurea;
49. 1-{4'-[2-ethoxy-3-(4-methylpiperid-1-yl)-3-oxopropyl]-3'-fluorobiphenyl-3-yl}-3-heptyl-1-methylurea;
50. 5-oxo-N-{4'-[2-ethoxy-3-(4-methylpiperid-1-yl)-3-oxopropyl]biphenyl-3-ylmethyl}-N-methylhexanoylamide;
51. {4'-[2-ethoxy-3-(4-methylpiperid-1-yl)-3-oxopropyl]biphenyl-3-ylmethyl}methylhexanoylamide;
52. 4-acetylamino-N-{4'-[2-ethoxy-3-(4-methylpiperid-1-yl)-3-oxopropyl]biphenyl-3-ylmethyl}-N-methylbutyramide;
53. N-{4'-[2-cyclopropylmethoxy-3-(4-methylpiperid-1-yl)-3-oxopropyl]biphenyl-3-ylmethyl}-N-methyloctanoylamide;
54. N-[4'-(2-cyclopropylmethoxy-3-morpholin-4-yl-3-oxopropyl)biphenyl-3-ylmethyl]-N-methyloctanoylamide;
55. N-[4'-(2-ethoxy-3-morpholin-4-yl-3-oxopropyl)biphenyl-3-ylmethyl]-N-methyloctanoylamid;
56. N-{4'-[2-ethoxy-3-(4-methylpiperid-1-yl)-3-oxopropyl]biphenyl-3-ylmethyl}-N-methyloctanoylamide;
57. N-[4'-(2-ethoxy-3-oxo-3-piperid-1-ylpropyl)biphenyl-3-ylmethyl]-N-methyloctanoylamide;
58. 1-[4'-(2-ethoxy-3-oxo-3-piperid-1-ylpropyl)biphenyl-3-yl]-3-heptyl-1-methylurea;
59. 1-{4'-[2-benzyloxy-3-(4-methylpiperid-1-yl)-3-oxopropyl]biphenyl-3-yl}-3-heptyl-1-methylurea;
60. 1-[4'-(2-benzyloxy-3-morpholin-4-yl-3-oxopropyl)biphenyl-3-yl]-3-heptyl-1-methylurea;
61. 1-[4'-(2-cyclopropylmethoxy-3-morpholin-4-yl-3-oxopropyl)biphenyl-3-yl]-3-heptyl-1-methylurea;
62. 1-[4'-(2-cyclopropylmethoxy-3-morpholin-4-yl-3-oxopropyl)biphenyl-3-yl]-1-methyl-3-pentylurea;
63. 1-[4'-(2-cyclopropylmethoxy-3-oxo-3-piperid-1-ylpropyl)biphenyl-3-yl]-1-methyl-3-pentylurea;
64. 1-[4'-(2-cyclopropylmethoxy-3-oxo-3-piperid-1-ylpropyl)biphenyl-3-yl]-3-heptyl-1-methylurea;
65. 1-{4'-[2-cyclopropylmethoxy-3-(4-methylpiperid-1-yl)-3-oxopropyl]biphenyl-3-yl}-3-heptyl-1-methylurea;
66. 3-heptyl-1-methyl-1-{4'-[3-(4-methylpiperid-1-yl)-3-oxo-2-propoxypropyl]biphenyl-3-yl}urea;
67. 1-methyl-1-[4'-(3-oxo-3-piperid-1-yl-2-propoxypropyl)biphenyl-3-yl]-3-pentylurea;
68. 3-heptyl-1-methyl-1-[4'-(3-oxo-3-piperid-1-yl-2-propoxypropyl)biphenyl-3-yl]urea.

According to the present invention, the compounds of formula (I) that are more particularly preferred are those having at least one of the following characteristics:

$R_1$ is an alkyl radical having from 1 to 12 carbon atoms or a sequence:
—$(CH_2)_m$—$(CO)_n$—$(X)_p$—$(CH_2)_q$—$R_5$ wherein m=1 or 2, n=0, p=0, q=0 and $R_5$ is an aralkyl radical, or a radical (a) in which $R_5$ is preferably hydrogen or a radical $COOR_6$;

$R_2$ is a radical of formula (a) in which $R_7$ is preferably an alkyl radical or a radical (b) in which $R_8$ is preferably a hydroxyl radical or a radical NR'R";

A is the linking radical of structure —$CH_2N(R_{12})$—CO or $N(R_{12})$—CO—$(D)_w$ in which w=0 or 1; and/or $R_4$ is an alkyl, aryl or heteroaryl radical.

Figure 2:
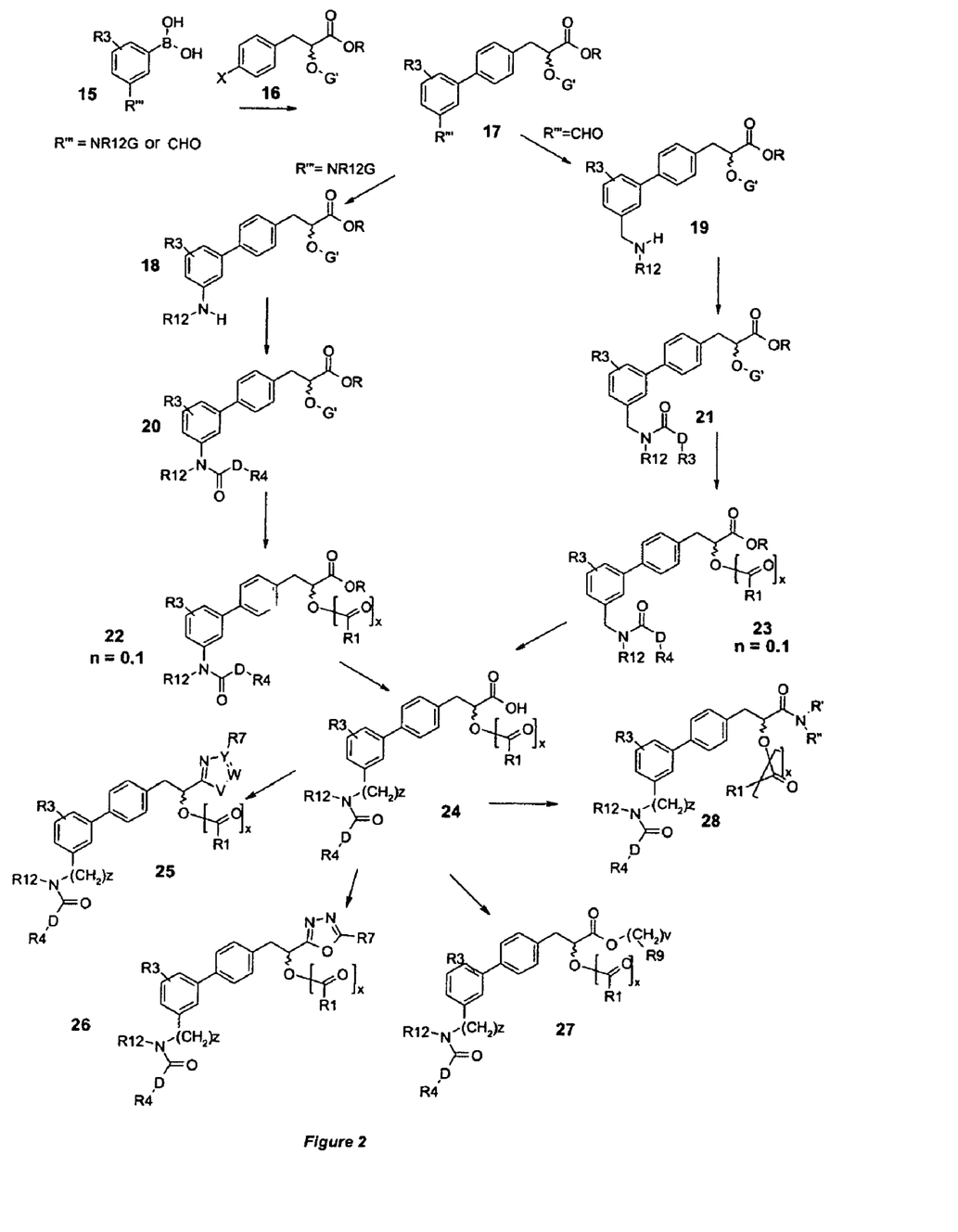

A general description of the preparation of the compounds of general formulae 10 to 14 and 24 to 28 of the attached FIGS. 1 and 2 is given below.

The remaining compounds of general formula (I) can be prepared from known compounds by the application or adaptation of known methods.

The reaction scheme described in FIG. 1 is a general scheme for obtaining derivatives in which R1 is an alkyl or aralkyl group.

The preparation of compound 2 is performed by coupling a chiral Evans reagent (for example (S)-4-benzyloxazolidin-2-one) and an alkoxy or aralkoxyacetyl chloride, preferably a commercially available one, in the presence of a base, for example butyllithium.

The intermediate 3 is obtained by a Suzuki coupling between 4-formylbenzeneboronic acid and a halogenated aromatic derivative (for example N-methyl-3-bromoaniline or N-methyl-3-bromobenzylamine, optionally protected with a group G).

The chiral intermediate 4 is obtained by enantioselective addition of compound 2 to the intermediate 3, in the presence of a boron derivative.

The production of compound 5 by dehydroxylation of compound 4 is performed by treatment with a trialkylsilane, for example triethylsilane, in an acidic medium, preferably in the presence of a Lewis acid such as boron trifluoroetherate, in dichloromethane, at 40° C.

The intermediates 8 and 9 may be prepared after deprotection of the amine (-G) by addition to an isocyanate if D=N or to an acid halide if D=C. Hydrolysis of the benzyloxazolidin-2-one portion to give compound 10 is performed under conditions allowing the stereochemistry of C—$OR_1$ to be conserved, for example with 1.5 equivalents of an aqueous 1M solution of lithium hydroxide in tetrahydrofuran, at room temperature.

The heterocyclic compounds 11 and 12 are synthesized by standard methods for synthesizing heterocycles, with, in the case of compound 12, condensation of butyric hydrazide and cyclization by heating to 105° C. in the presence of phosphorus oxychloride.

The esters 13 may be prepared, for example, by esterification with alcohols $HO(CH_2)_vR_9$.

The compounds 14 are obtained by amidation reaction with an amine of the type HNR'R".

To obtain derivatives with greater diversity as regards the groups $R_1$ introduced, the synthetic route described in FIG. 2 is used.

The boronic acid 15 is obtained according to the standard method starting with optionally protected N-alkyl-3-bromoaniline or 3-bromobenzaldehyde.

Compound 16 is obtained according to the scheme described in FIG. 3 starting with the halogenated amino acid 29, for example 4-bromophenylalanine. The conversion into the keto acid 30 may be performed, for example, by formation of a Schiff's base between compound 29 and isonicotinaldehyde, followed by conversion to a keto derivative by treatment with 1,8-diazobicyclo[5.4.0]undec-7-ene (DBU) in methanol, followed by an acid hydrolysis of the intermediate species (Synthesis, 1982, 756). The intermediate 31 is prepared by enantioselective reduction of the keto acid 30, for example, in the presence of sodium borohydride and D-tartaric acid. Treatment of the α-hydroxy acid compound 31 with a silyl halide (for example tert-butyldimethylsilyl chloride) gives compound 32. By formation of an ester, for example a benzyl ester, intermediate 16 is obtained.

A Suzuki coupling catalyzed, for example, with tetrakis (triphenylphosphine)palladium between compounds 15 and 16 produces the intermediate 17.

In the case where R'"=CHO, compound 19 is prepared by a reductive amination reaction with an amine $H_2NR_{12}$.

Compounds 20 and 21 are obtained after deprotection of the amine (if necessary) by addition to an isocyanate $R_4N$=C=O or condensation with an acid or an acid halide.

The derivatives 22 and 23 for which x=0 are prepared after deprotection of the alcohol (-G') via a Mitsunobu reaction on an alcohol $R_1OH$ (more particularly a phenol) or via alkylation with a halogenated derivative $R_1X$ in the presence of silver oxide, for example.

The derivatives 22 and 23 for which x=1 are obtained by coupling with an acid $R_1CO_2H$ or an acid halide $R_1COX$.

The hydrolysis of the esters 22 and 23 is performed according to standard methods allowing the stereochemistry to be conserved, for example by hydrogenation in the presence of palladium-on-charcoal in the case of benzyl esters. Compound 24 thus obtained is converted into compounds 25, 26, 27 and 28 according to the methods successively described for the production of the derivatives 11, 12, 13 and 14.

The compounds according to the invention show modulatory properties on receptors of PPAR type. This activity on the PPARα, δ and γ receptors is measured in a transactivation test and quantified via the dissociation constant Kdapp (apparent), as described in Example 8.

The preferred compounds of the present invention have a dissociation constant of less than or equal to 1000 nM and advantageously less than or equal to 500 nM.

Preferably, the compounds are modulators of receptors of specific PPARγ type, i.e., they have a ratio between the Kdapp for the PPARα and PPARδ receptors, and the Kdapp for the PPARγ receptors, of greater than or equal to 10. Preferably, this ratio PPARγ/PPARα or PPARγ/PPARδ is greater than or equal to 50 and more advantageously greater than or equal to 100.

The present invention also features medicinal products, comprising the compounds of formula (I) as described above.

The present invention also features administration of the compounds of formula (I) for regulating and/or restoring the metabolism of skin lipids.

The compounds according to the invention are particularly suitable in the following fields of treatment:

1) for treating dermatological afflictions or conditions associated with a keratinization disorder relating to differentiation and to proliferation, in particular for treating common acne, comedones, polymorphs, rosacea, nodulocystic acne, acne conglobata, senile acne and secondary acne such as solar, medicinal or occupational acne,
2) for treating other types of keratinization disorder, in particular ichthyosis, ichthyosiform conditions, Darrier's disease, palmoplantar keratoderma, leukoplakia and leukoplakiform conditions, and cutaneous or mucous (oral) lichen,
3) for treating other dermatological afflictions or conditions having an inflammatory immuno-allergic component, with or without a cellular proliferation disorder, and in particular all forms of psoriasis, whether cutaneous, mucous or ungual psoriasis, and even arthropathia psoriatica, or alternatively cutaneous atopy such as eczema, or respiratory atopy or gingival hypertrophy,
4) for treating all dermal or epidermal proliferations, whether benign or malignant, whether or not of viral origin, such as common warts, flat warts and epidermodysplasia verruciformis, oral or florid papillomatoses, T lymphoma and proliferations which may be induced by ultraviolet light, in particular in the case of basal cell and spinocellular epithelioma, and also any precancerous skin lesion such as keratoacanthomas,
5) for treating other dermatological disorders such as immune dermatitides, such as lupus erythematosus, bullous immune diseases and collagen diseases, such as scleroderma,
6) in the treatment of dermatological or systemic afflictions or conditions having an immunological component,
7) in the treatment of skin disorders due to exposure to UV radiation, and also for repairing or combating aging of the skin, whether light-induced or chronological aging, or for reducing actinic keratoses and pigmentations, or any pathology associated with chronological or actinic aging, such as xerosis,
8) for combating sebaceous function disorders such as the hyperseborrhoea of acne or simple seborrhoea or seborrhoeic dermatitis,
9) for preventing or treating cicatrization disorders or for preventing or repairing stretch marks,
10) in the treatment of pigmentation disorders, such as hyperpigmentation, melasma, hypopigmentation or vitiligo,
11) in the treatment of lipid metabolism afflictions or conditions, such as obesity, hyperlipidaemia, non-insulin-dependent diabetes or syndrome X,
12) in the treatment of inflammatory afflictions or conditions, such as arthritis,
13) in the treatment or prevention of cancerous or precancerous conditions,
14) in the prevention or treatment of alopecia of various origins, in particular alopecia caused by chemotherapy or radiation,
15) in the treatment of immune system disorders, such as asthma, type I sugar diabetes, multiple sclerosis or other selective dysfunctions of the immune system, or
16) in the treatment of afflictions or conditions of the cardiovascular system, such as arteriosclerosis or hypertension.

The present invention also features pharmaceutical or cosmetic compositions comprising, in a physiologically acceptable medium, at least one compound of formula (I) as defined above.

The compositions according to the invention may be administered enterally, parenterally, topically or ocularly. The pharmaceutical composition is preferably packaged in a form which is suitable for topical application.

Via the enteral route, the composition, more particularly the pharmaceutical composition, may be in the form of tablets, gel capsules, sugar-coated tablets, syrups, suspensions, solutions, powders, granules, emulsions or lipid or polymer vesicles or nanospheres or microspheres to allow controlled release. Via the parenteral route, the composition may be in the form of solutions or suspensions for infusion or for injection.

The compounds according to the invention are generally administered at a daily dose of about 0.001 mg/kg to 100 mg/kg of body weight in 1 to 3 dosage intakes.

The compounds are used systemically at a concentration generally from 0.001% to 10% by weight and preferably from 0.01% to 1% by weight relative to the weight of the composition.

Via the topical route, the pharmaceutical composition according to the invention is more particularly intended for treating the skin and mucous membranes and may be in the form of ointments, creams, milks, salves, powders, impregnated pads, syndets solutions, gels, sprays, foams, suspensions, stick lotions, shampoos or washing bases. It may also be in the form of suspensions of lipid or polymer vesicles or nanospheres or microspheres or polymer patches and hydrogels to allow controlled release. This topical-route composition may be in anhydrous form, in aqueous form or in the form of an emulsion.

The compounds are used topically at a concentration generally from 0.001% to 10% by weight, preferably from 0.01% to 1% by weight relative to the total weight of the composition.

The compounds of formula (I) according to the invention also find an application in the cosmetic field, in particular in body and hair hygiene and more particularly for regulating and/or restoring skin lipid metabolism.

This invention therefore also features the cosmetic use of a composition comprising, in a physiologically acceptable support, at least one of the compounds of formula (I) for body or hair hygiene.

The cosmetic composition according to the invention containing, in a cosmetically acceptable support, at least one compound of formula (I) or an optical or geometrical isomer or salt thereof, may usually be in the form of a cream, a milk, a lotion, a gel, suspensions of lipid or polymer vesicles or nanospheres or microspheres, impregnated pads, solutions, sprays, mousses, sticks, soaps, shampoos or washing bases.

The concentration of compound of formula (I) in the cosmetic composition is from 0.001% to 3% by weight relative to the total weight of the composition.

The pharmaceutical and cosmetic compositions as described above may also contain inert or even pharmacodynamically active additives as regards the pharmaceutical compositions, or combinations of these additives, and especially:

wetting agents;
flavor enhancers;
preservatives such as para-hydroxybenzoic acid esters;
stabilizers;
humidity regulators;
pH regulators;
osmotic pressure modifiers;
emulsifiers;
UV-A and UV-B screening agents;
antioxidants, such as α-tocopherol, butylhydroxyanisole or butylhydroxytoluene, superoxide dismutase, ubiquinol or certain metal-chelating agents;
depigmenting agents such as hydroquinone, azelaic acid, caffeic acid or kojic acid;
emollients;
moisturizers, for instance glycerol, PEG 400, thiamorpholinone and derivatives thereof, or urea;
antiseborrhoeic or antiacne agents, such as S-carboxymethylcysteine, S-benzylcysteamine, salts thereof or derivatives thereof, or benzoyl peroxide;
antibiotics, for instance erythromycin and its esters, neomycin, clindamycin and its esters, and tetracyclines;
antifungal agents such as ketoconazole or polymethylene-4,5-isothiazolidones-3;
agents for promoting regrowth of the hair, for instance Minoxidil (2,4-diamino-6-piperidinopyrimidine 3-oxide) and its derivatives, Diazoxide (7-chloro-3-methyl-1,2,4-benzothiadiazine 1,1-dioxide) and Phenyloin (5,4-diphenylimidazolidine-2,4-dione);
non-steroidal anti-inflammatory agents;
carotenoids, and especially β-carotene;
antipsoriatic agents such as anthraline and its derivatives;
eicosa-5,8,11,14-tetraynoic acid and eicosa-5,8,11-triynoic acid, and esters and amides thereof;
retinoids, i.e., RAR or RXR receptor ligands, which may be natural or synthetic;
corticosteroids or oestrogens;
α-hydroxy acids and α-keto acids or derivatives thereof, such as lactic acid, malic acid, citric acid, glycolic acid, mandelic acid, tartaric acid, glyceric acid or ascorbic acid, and also the salts, amides or esters thereof, or β-hydroxy acids or derivatives thereof, such as salicylic acid and the salts, amides or esters thereof;
ion-channel blockers such as potassium-channel blockers;
or alternatively, more particularly for the pharmaceutical compositions, in combination with medicinal products known to interfere with the immune system (for example cyclosporin, FK 506, glucocorticoids, monoclonal antibodies, cytokines or growth factors, etc.).

Needless to say, one skilled in this art will take care to select the optional compound(s) to be added to these compositions such that the advantageous properties intrinsically associated with the present invention are not, or are not substantially, adversely affected by the envisaged addition.

Several examples of the production of active compounds of formula (I) according to the invention, and also biological activity results for such compounds and various specific formulations based on its compounds will now be given, it being understood that same are intended only as illustrative and in nowise limitative. In said examples to follow, all parts and percentages are given by weight, unless otherwise indicated.

EXAMPLE 1

Synthesis of N-{4'-[2-ethoxy-2-(5-propyl[1,3,4] oxadiazol-2-yl)ethyl]biphenyl-3-ylmethyl}-N-methyl-6-(2-methoxyethoxymethoxy)naphthalene-2-carboxylamide (a) Preparation of tert-butyl (3-bromobenzyl)carbamate:

40 g (183 mmol) of di-tert-butyl dicarbonate are added portionwise, at room temperature, to a mixture of 40.7 g (183 mmol) of 3-bromobenzylamine hydrochloride, 26 ml of triethylamine (183 mmol) and 450 ml of dichloromethane. After stirring for 18 hours, the reaction medium is poured into ice-cold water and extracted with dichloromethane. The organic phase is separated out by settling of the phases, dried over magnesium sulfate and evaporated. 46 g of tert-butyl (3-bromobenzyl)carbamate are obtained in a yield of 88%.

(b) Preparation of tert-butyl (3-bromobenzyl)-N-methylcarbamate:

19 g (475 mmol) of sodium hydride (60% in oil) are added portionwise to a solution of 128 g (447 mmol) of tert-butyl (3-bromobenzyl)carbamate in 800 ml of DMF, and the reaction medium is stirred until the evolution of gas has ceased. 29.3 ml (470 mmol) of methyl iodide are added dropwise and stirring is continued for 18 hours. The reaction medium is poured into ice-cold water and extracted with ethyl acetate. The organic phase is separated out by settling of the phases, dried over magnesium sulfate and evaporated. 152.5 g of tert-butyl (3-bromobenzyl)-N-methylcarbamate are obtained in a yield of 92%.

(c) Preparation of tert-butyl (4'-formyidiphenyl-3-ylmethyl)methylcarbamate:

307 ml (615 mmol) of aqueous potassium carbonate solution (2M) are added dropwise to a mixture of 61.5 g (205 mmol) of tert-butyl (3-bromobenzyl)-N-methylcarbamate, 46 g (307 mmol) of 4-formylbenzeneboronic acid and 500 ml of toluene. The reaction medium is then degassed with argon and 7 g (6.2 mmol) of tetrakis(triphenylphosphine) palladium(0) are added. After heating at 90° C. for 24 hours, the reaction medium is poured into water and extracted with ethyl acetate. The organic phase is separated out by settling of the phases, dried over magnesium sulfate and evaporated. The residue obtained is purified by chromatography on a column of silica eluted with a mixture of heptane and ethyl acetate (70/30). After evaporating off the solvents, 67 g of tert-butyl (4'-formylbiphenyl-3-ylmethyl)methylcarbamate are collected in a yield of 60%.

(d) Preparation of tert-butyl (N-{4'-[3-(4-benzyl-2-oxooxazolidin-3-yl)-2-ethoxy-1-hydroxy-3-oxopropyl]biphenyl-3-ylmethyl}-N-methylcarbamate:

138 ml (138 mmol) of a 1M solution of dibutylborane triflate in dichloromethane are added dropwise to a solution of 29 g (111 mmol) of (S)-4-benzyl-3-(2-ethoxyacetyl)oxazolidin-2-one (prepared as described in the publication by Bernard Hulin et al., *J. Med. Chem.*, 1996, 39, 3897-3907, starting with commercial (S)-4-benzyloxazolidin-2-one) cooled to 0° C., followed by addition of 24 ml (138 mmol) of diisopropylethylamine. The reaction medium is stirred for 30 minutes at 0° C. and then cooled to −78° C. and 30 g (92 mmol) of tert-butyl (4'-formylbiphenyl-3-ylmethyl)methylcarbamate diluted in 250 ml of dichloromethane are added dropwise. The reaction medium is stirred from −78° C. to room temperature over 2 hours. After returning to 0° C., 250 ml of a pH 7 buffer solution diluted with 250 ml of methanol and then 250 ml of an aqueous 30% hydrogen peroxide solution diluted with 250 ml of methanol are added dropwise to the reaction medium, and stirring is continued at 0° C. for 1 hour 30 minutes. After extraction with dichloromethane, washing with water, drying over magnesium sulfate and evaporating off the solvent, 80 g of crude product are obtained. The residue is purified by chromatography on a column of silica eluted with a heptane/ethyl acetate mixture of polarity increasing from 8/2 to 6/4. 54 g of tert-butyl (N-{4'-[3-(4-benzyl-2-oxooxazolidin-3-yl)-2-ethoxy-1-hydroxy-3-oxopropyl]biphenyl-3-ylmethyl}-N-methylcarbamate are obtained in a yield of 70%.

(e) Preparation of 4-benzyl-3-[2-ethoxy-3-(3'-methylaminomethylbiphenyl-4-yl)propionyl]oxazolidin-2-one:

43 ml (272 mmol) of triethylsilane are added dropwise to a solution of 17 ml (136 mmol) of boron trifluoroetherate in 150 ml of dichloromethane cooled beforehand to 0° C. After stirring for 15 minutes, 10 g (17 mmol) of tert-butyl N-{4'-[3-(4-benzyl-2-oxooxazolidin-3-yl)-2-ethoxy-1-hydroxy-3-oxopropyl]biphenyl-3-ylmethyl}-N-methylcarbamate dissolved in 70 ml of dichloromethane are added dropwise. The reaction medium is stirred from 0° C. to room temperature for 3 hours and then heated at 40° C. for 48 hours, treated with saturated aqueous sodium carbonate solution, extracted with dichloromethane, dried over magnesium sulfate, filtered and concentrated. The residue obtained is purified by chromatography on a column of silica eluted with a dichloromethane/methanol/triethylamine mixture (95/5/0.5). 8 g of 4-benzyl-3-[2-ethoxy-3-(3'-methylaminomethylbiphenyl-4-yl)propionyl]oxazolidin-2-one are obtained in a yield of 13% to 3 g of methyl 2-ethoxy-3-hydroxy-3-(3'-methylaminomethylbiphenyl-4-yl)propionate are obtained in a yield of 51%.

(f) Preparation of methyl 2-ethoxy-3-(3'-methylaminomethylbiphenyl-4-yl)propionate:

In a manner similar to that of Example 1(e), starting with 3 g (9 mmol) of methyl 2-ethoxy-3-hydroxy-3-(3'-methylaminomethylbiphenyl-4-yl)propionate, 0.6 g of methyl 2-ethoxy-3-(3'-methylaminomethylbiphenyl-4-yl)propionate are obtained in a yield of 21%.

(g) Preparation of methyl 3-(3'-[{(tert-butoxycarbonylmethylamino)methyl]biphenyl-4-yl)-2-ethoxypropionate:

A solution of 0.4 g (1.9 mmol) of di-tert-butyl carbonate in 5 ml of dichloromethane is added dropwise to a solution of 0.6 g (1.9 mmol) of methyl 2-ethoxy-3-(3'-methylaminomethylbiphenyl-4-yl)propionate and 0.25 ml (1.9 mmol) of triethylamine in 10 ml of dichloromethane. After stirring at room temperature for 48 hours, the medium is washed with water, extracted with dichloromethane, dried over magnesium sulfate, filtered and evaporated to dryness. The residue obtained is purified by chromatography on a column of silica eluted with a 9/1 heptane/ethyl acetate mixture. 0.78 g of methyl 3-{3'-[(tert-butoxycarbonylmethylamino)methyl]biphenyl-4-yl}-2-ethoxypropionate is obtained in a yield of 85%.

(h) Preparation of 3-(3{'-[(tert-butoxycarbonylmethylamino)methyl]biphenyl-4-yl}-2-ethoxypropionic acid:

0.65 g (1.3 mmol) of methyl 3-{3'-[(tert-butoxycarbonylmethylamino)methyl]biphenyl-4-yl}-2-ethoxypropionate is placed in 10 ml of tetrahydrofuran, 0.5 ml of methanol and 1.9 ml (1.9 mmol) of aqueous 1M lithium hydroxide solution. After stirring at room temperature for 2 hours, the reaction medium is diluted with ethyl acetate, acidified to pH 6 with aqueous 1N hydrochloric acid solution, extracted with ethyl acetate, dried over magnesium sulfate, filtered and concentrated. 0.54 g of 3-{3'-[(tert-butoxycarbonylmethylamino)methyl]biphenyl-4-yl}-2-ethoxypropionic acid is obtained in a yield of 92%.

(i) Preparation of tert-butyl N-{4'-[3-(N'-butyiylhydrazino)-2-ethoxy-3-oxopropyl]biphenyl-3-ylmethyl}-N-methylcarbamate:

0.15 ml (1.33 mmol) of N-methylmorpholine is added to a solution of 0.5 g (1.2 mmol) of 3-{3'-[(tert-butoxycarbonylmethylamino)methyl]-biphenyl-4-yl}-2-ethoxypropionic acid, 0.14 g (1.3 mmol) of butyric hydrazide and 0.33 g (2.4 mmol) of 1-hydroxybenzotriazole in 10 ml of tetrahydrofuran cooled to −5° C. After stirring for 5 minutes, 0.2 ml (1.3 mmol) of diisopropylcarbodiimide is added. The reaction medium is stirred at 0° C. for 1 hour and then at room temperature for 2 hours, diluted with ethyl acetate, washed with saturated aqueous caesium hydrogen carbonate solution, extracted with ethyl acetate, dried over magnesium sulfate, filtered and concentrated. The residue obtained is chromatographed on a column of silica eluted with a 1/1 heptane/ethyl acetate mixture. 0.6 g of tert-butyl N-{4'-[3-(N'-butyrylhydrazino)-2-ethoxy-3-oxopropyl]biphenyl-3-ylmethyl}-N-methylcarbamate is obtained in a yield of 100%.

(j) Preparation of {4'-[2-ethoxy-2-(5-propyl[1,3,4]oxadiazol-2-yl)ethyl]biphenyl-3-ylmethyl}methylamine:

0.6 g (1.2 mmol) of tert-butyl N-{4'-[3-(N'-butyrylhydrazino)-2-ethoxy-3-oxopropyl]biphenyl-3-ylmethyl}-N-methylcarbamate is placed in 1.5 ml of phosphorus oxychloride and heated at 105° C. for 30 minutes. The reaction medium is cooled and then treated cautiously with aqueous 28% ammonia solution until the pH is equal to 8, diluted with dichloromethane and washed with water. After separation of the phases by settling, the organic phase is dried over magnesium sulfate and concentrated. The residue obtained is purified on a column of silica eluted with a mixture of dichloromethane/methanol/a few drops of aqueous ammonia with a polarity gradient from 9/1 to 7/3. 0.2 g of {4'-[2-ethoxy-2-(5-propyl[1,3,4]oxadiazol-2-yl)ethyl]biphenyl-3-ylmethyl}methylamine is obtained in a yield of 43%.

(k) Synthesis of N-{4'-[2-Ethoxy-2-(5-propyl[1,3,4]oxadiazol-2-yl)ethyl]biphenyl-3-ylmethyl}-N-methyl-6-(2-methoxyethoxymethoxy)naphthalene-2-carboxylamide:

0.045 g (0.12 mmol) of HATU, 0.11 g (0.16 mmol) of PS-carbodiimide resin and 0.2 ml (0.053 mmol) of a solution of {4'-[2-ethoxy-2-(5-propyl[1,3,4]oxadiazol-2-yl)ethyl]biphenyl-3-ylmethyl}methylamine in dichloromethane (solution concentration: 200 mg/2 ml of dichloromethane) are successively added to a solution of 22 mg (0.08 mmol) of 6-(2-methoxyethoxymethoxy)naphthalene-2-carboxylic acid in 0.3 ml of dichloromethane and 0.3 ml of dimethylformamide. The reaction medium is stirred at room temperature for 18 hours and then filtered and the solvents are evaporated off. The residue obtained is placed in 0.3 ml of dichloromethane and 0.3 ml of dimethylformamide, and 180 mg (0.48 mmol) of MP-carbonate resin are added. After stirring for 5 hours, the resin is filtered off and the solvents are evaporated off. 36 mg of N-{4'-[2-ethoxy-2-(5-propyl[1,3,4]oxadiazol-2-yl)ethyl]biphenyl-3-ylmethyl}-N-methyl-6-(2-methoxyethoxymethoxy)naphthalene-2-carboxylamide are obtained in a quantitative yield.

HPLC Hypersil Thermoquest, Hypurity Elite C18, 3 microns, 2.1×150 mm, ($CH_3CN/HCOOH/H_2O$: 5/0.01/5), flow rate: 0.5 ml/minute, retention time: 17.8 minutes, purity: 74%, ESMS m/z 638.3 $(M+H)^+$

EXAMPLE 2

Synthesis of N-{4'-[2-ethoxy-2-(5-propyl[1,3,4]oxadiazol-2-yl)ethyl]biphenyl-3-ylmethyl}-N-methyl-4-phenoxybenzamide In a manner similar to that of Example 1(k), starting with 17 mg (0.08 mmol) of 4-phenoxybenzoic acid and 0.2 ml (0.053 mmol) of a solution of {4'-[2-ethoxy-2-(5-propyl[1,3,4]oxadiazol-2-yl)ethyl]biphenyl-3-ylmethyl}methylamine in dichloromethane (solution concentration: 200 mg/2 ml of dichloromethane), 35 mg of N-{4'-[2-ethoxy-2-(5-propyl[1,3,4]oxadiazol-2-yl)ethyl]biphenyl-3-ylmethyl}-N-methyl-4-phenoxybenzamide are obtained in a quantitative yield.

HPLC Hypersil Thermoquest, Hypurity Elite C18, 3 microns, 2.1×150 mm, ($CH_3CN/HCOOH/H_2O$: 5/0.01/5), flow rate: 0.5 ml/minute, retention time: 19.3 minutes, purity: 84%, ESMS m/z 576.2 $(M+H)^+$

EXAMPLE 3

Synthesis of N-{4'-[2-ethoxy-2-(5-propyl[1,3,4]oxadiazol-2-yl)ethyl]biphenyl-3-ylmethyl}-N-methyloctane-1-carboxylamide 20 µl (0.11 mmol) of octanoyl chloride are added to a mixture of 0.3 ml of tetrahydrofuran, 0.2 ml (0.053 mmol) of a solution of {4'-[2-ethoxy-2-(5-propyl[1,3,4]oxadiazol-2-yl)ethyl]biphenyl-3-ylmethyl}methylamine in tetrahydrofuran (solution concentration: 200 mg/2 ml of tetrahydrofuran) and 0.1 ml (0.06 mmol) of a solution of triethylamine in tetrahydrofuran (concentration: 0.1 ml/1 ml of tetrahydrofuran). The reaction medium is stirred at room temperature for 20 hours and then filtered and the solvents are evaporated off. The residue obtained is placed in 0.5 ml of tetrahydrofuran and 0.2 ml of dichloromethane, and 125 mg of AP-trisamine resin (0.55 mmol) are added. After stirring for 4 hours, the resin is filtered off and the solvents are evaporated off. 13 mg of N-{4'-[2-ethoxy-2-(5-propyl[1,3,4]oxadiazol-2-yl)ethyl]biphenyl-3-ylmethyl}-N-methyloctane-1-carboxylamide are obtained in a yield of 50%.

HPLC Hypersil Thermoquest, Hypurity Elite C18, 3 microns, 2.1×150 mm, ($CH_3CN/HCOOH/H_2O$: 5/0.01/5), flow rate: 0.5 ml/minute, retention time: 23.8 minutes, purity: 92%, ESMS m/z 506.2 $(M+H)^+$

EXAMPLE 4

Synthesis of N-{4'-[2-ethoxy-2-(5-propyl[1,3,4]oxadiazol-2-yl)ethyl]biphenyl-3-ylmethyl}-N-methylbiphenyl-4-carboxylamide In a manner similar to that of Example 3, starting with 0.2 ml (0.053 mmol) of a solution of {4'-[2-ethoxy-2-(5-propyl[1,3,4]oxadiazol-2-yl)ethyl]biphenyl-3-ylmethyl}methylamine, 0.2 ml (0.12 mmol) of a solution of triethylamine in tetrahydrofuran (concentration: 0.1 ml/1 ml of tetrahydrofuran) and 48 mg (0.11 mmol) of biphenyl-4-carbonyl chloride, 8 mg of N-{4'-[2-ethoxy-2-(5-propyl[1,3,4]oxadiazol-2-yl)ethyl]biphenyl-3-ylmethyl}-N-methyl-biphenyl-4-carboxylamide are obtained in a yield of 30%.

HPLC Hypersil Thermoquest, Hypurity Elite C18, 3 microns, 2.1×150 mm, ($CH_3CN/HCOOH/H_2O$: 5/0.01/5), flow rate: 0.5 ml/minute, retention time: 19.3 minutes, purity: 89%, ESMS m/z 560.2 $(M+H)^+$

EXAMPLE 5

Synthesis of N-{4'-[2-ethoxy-2-(5-propyl[1,3,4]oxadiazol-2-yl)ethyl]biphenyl-3-ylmethyl}-N-methyl-6-propoxynaphthalene-2-carboxylamide In a manner similar to that of Example 1(k), starting with 18 mg (0.08 mmol) of 6-propoxynapthalene-2-carboxylic acid and 0.2 ml (0.053 mmol) of a solution of {4'-[2-ethoxy-2-(5-propyl[1,3,4]oxadiazol-2-yl)ethyl]biphenyl-3-ylmethyl}methylamine in dichloromethane (solution concentration: 200 mg/2 ml of dichloromethane), 15 mg of N-{4'-[2-ethoxy-2-(5-propyl[1,3,4]oxadiazol-2-yl)ethyl]biphenyl-3-ylmethyl}-N-methyl-6-propoxynaphthalene-2-carboxylamide are obtained in a yield of 50%.

HPLC Hypersil Thermoquest, Hypurity Elite C18, 3 microns, 2.1×150 mm, ($CH_3CN/HCOOH/H_2O$: 5/0.01/5), flow rate: 0.5 ml/minute, retention time: 22.3 minutes, purity: 84%, ESMS m/z 592.4 $(M+H)^+$

EXAMPLE 6

Synthesis of N-{4'-[2-ethoxy-2-(5-propyl[1,3,4]oxadiazol-2-yl)ethyl]biphenyl-3-ylmethyl}-N-methyl-4'-(2-methoxyethoxymethoxymethyl)biphenyl-4-carboxylamide In a manner similar to that of Example 1(k), starting with 22 mg (0.08 mmol) of 4'-(2-methoxyethoxymethoxy)biphenyl-4-carboxylic acid and 0.2 ml (0.053 mmol) of a solution of {4'-[2-ethoxy-2-(5-propyl[1,3,4]oxadiazol-2-yl)ethyl]biphenyl-3-ylmethyl}methylamine in dichloromethane (solution concentration: 200 mg/2 ml of dichloromethane), 15 mg of N-{4'-[2-ethoxy-2-(5-propyl[1,3,4]oxadiazol-2-yl)ethyl]biphenyl-3-ylmethyl}-N-methyl-4'-(2-methoxyethoxymethoxymethyl)biphenyl-4-carboxylamide are obtained in a yield of 50%.

HPLC Hypersil Thermoquest, Hypurity Elite C18, 3 microns, 2.1×150 mm, ($CH_3CN/HCOOH/H_2O$: 5/0.01/5), flow rate: 0.5 ml/minute, retention time: 21 minutes, purity: 83%, ESMS m/z 665.4 $(M+H)^+$

EXAMPLE 7

Synthesis of methyl 6-({4'-[2-ethoxy-2-(5-propyl[1,3,4]oxadiazol-2-yl)ethyl]biphenyl-3-ylmethyl}methylcarbamoyl)naphthalene-2-carboxylate In a manner similar to that of Example 1(k) starting with 18 mg (0.08 mmol) of naphthalene-2,4-dicarboxylic acid monomethyl ester and 0.2 ml (0.053 mmol) of a solution of {4'-[2-ethoxy-2-(5-propyl[1,3,4]oxadiazol-2-yl)ethyl]biphenyl-3-ylmethyl}methylamine in dichloromethane (solution concentration: 200 mg/2 ml of dichloromethane), 19 mg of methyl 6-({4'-[2-ethoxy-2-(5-propyl[1,3,4]oxadiazol-2- yl)ethyl]biphenyl-3-ylmethyl}methylcarbamoyl)naphthalene-2-carboxylate are obtained in a yield of 60%.

HPLC Hypersil Thermoquest, Hypurity Elite C18, 3 microns, 2.1×150 mm, (CH$_3$CN/HCOOH/H$_2$O: 5/0.01/5), flow rate: 0.5 ml/minute, retention time: 20.4 minutes, purity: 99%, ESMS m/z 592.3 (M+H)$^+$

EXAMPLE 8

Crossed-Curve PPAR Transactivation Test

The activation of receptors with an agonist (activator) in HeLN cells leads to the expression of a reporter gene, luciferase, which, in the presence of a substrate, generates light. The modulation of the receptors is measured by quantifying the luminescence produced after incubating the cells in the presence of a reference agonist. The ligands displace the agonist from its site. The measurement of the activity is performed by quantifying the light produced. This measurement makes it possible to determine the modulatory activity of the compounds according to the invention by determining the constant that is the affinity of the molecule for the receptor. Since this value can fluctuate depending on the basal activity and the expression of the receptor, it is referred to as Kd apparent (KdApp in nM).

To determine this constant, "crossed curves" of the test product against a reference agonist are performed in a 96-well plate: 10 concentrations of the test product plus a concentration 0 are arranged in a line, and 7 concentrations of the agonist plus a concentration 0 are arranged in a column. This is 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluorophenyl)-1-heptylureido]ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{4-[2-(methylpyrid-2-ylamino)ethoxy]benzyl}thiazolidine-2,4-dione for PPARγ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are inoculated into 96-well plates at a rate of 10 000 cells per well in 100 μl of DMEM medium without phenol red and supplemented with 10% of defalted calf serum. The plates are then incubated at 37° C. and 7% CO$_2$ for 16 hours.

The various dilutions of the test products and of the reference ligand are added at a rate of 5 μl per well. The plates are then incubated for 18 hours at 37° C. and 7% CO$_2$. The culture medium is removed by turning over and 100 μl of a 1:1 PBS/luciferine mixture are added to each well. After 5 minutes, the plates are read by the luminescence detector.

These crossed curves make it possible to determine the AC50 values (concentration at which 50% activation is observed) of the reference ligand at various concentrations of test product. These AC50 values are used to calculate the Schild regression by plotting a straight line corresponding to the Schild equation ("quantitation in receptor pharmacology" Terry P. Kenakin, *Receptors and Channels*, 2001, 7, 371-385) which allows the Kd app values (in nM) to be obtained.

Transactivation Results:

| Compounds | PPARα Kd app (nM) | PPARδ Kd app (in nM) | PPARγ Kd app (in nM) |
|---|---|---|---|
| Reference 1: 2-(4-(2-[3-(2,4-difluorophenyl)-1-heptylureido]-ethyl}phenylsulfanyl)-2-methylpropionic acid | 200 | n.a. | n.a. |
| Reference 2: {2-methyl-4-[4-methyl-2-(4-trifluoromethylphenyl)thiazol-5-ylmethylsulfanyl]phenoxy}acetic acid | n.a. | 10 | n.a. |
| Reference 3: 5-{4-[2-(methylpyrid-2-ylamino)ethoxy]benzyl}thiazolidine-2,4-dione | n.a. | n.a. | 30 |
| Example 1 | n.a. | n.a. | 250 |
| Example 2 | n.a. | n.a. | 1000 |
| Example 7 | n.a. | n.a. | 250 | n.a. means not active

These results show the affinity of the compounds for PPAR-γ and more particularly the specificity of the affinity of the compounds of the invention for the PPARγ subtype, compared with the affinity of the compounds for the PPARα subtype or for the PPARδ subtype.

EXAMPLE 9

Compositions

Various specific formulations based on the compounds according to the invention are illustrated in this example.

A. Oral Route:

(a) 0.2 g tablet:

| | |
|---|---|
| Compound of Example 2 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampules:

| | |
|---|---|
| Compound of Example 7 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g tablet:

| | |
|---|---|
| Compound of Example 1 | 0.500 g |
| Pregelatinized starch | 0.100 g |
| Microcrystalline cellulose | 0.115 g |
| Lactose | 0.070 g |
| Magnesium stearate | 0.010 g |

(d) Drinkable suspension in 10 ml ampules:

| | |
|---|---|
| Compound of Example 1 | 0.200 g |
| Glycerol | 1.000 g |
| 70% Sorbitol | 1.000 g |
| Sodium saccharinate | 0.010 g |
| Methyl para-hydroxybenzoate | 0.080 g |
| Flavoring | qs |
| Purified | qs 10 ml |

B. Topical Route:

(a) Ointment:

| | |
|---|---|
| Compound of Example 1 | 0.020 g |
| Isopropyl myristate | 81.700 g |
| Liquid petroleum jelly fluid | 9.100 g |
| Silica ("Aerosil 200" sold by Degussa) | 9.180 g |

(b) Ointment:

| | |
|---|---|
| Compound of Example 2 | 0.300 g |
| White petroleum jelly codex | qs 100 g |

(c) Nonionic water-in-oil cream:

| | |
|---|---|
| Compound of Example 7 | 0.100 g |
| Mixture of emulsifying lanolin alcohols, waxes and oils ("Anhydrous Eucerin" sold by BDF) | 39.900 g |
| Methyl para-hydroxybenzoate | 0.075 g |
| Propyl para-hydroxybenzoate | 0.075 g |
| Sterile demineralized | qs 100 g |

(d) Lotion:

| | |
|---|---|
| Compound of Example 7 | 0.100 g |
| Polyethylene glycol (PEG 400) | 69.900 g |
| 95% Ethanol | 30.000 g |

(e) Hydrophobic ointment:

| | |
|---|---|
| Compound of Example 1 | 0.300 g |
| Isopropyl myristate | 36.400 g |
| Silicone oil ("Rhodorsil 47 V 300" sold by Rhone-Poulenc) | 36.400 g |
| Beeswax | 13.600 g |
| Silicone oil ("Abil 300,000 cst" sold by Goldschmidt) | qs 100 g |

(f) Nonionic oil-in-water cream:

| | |
|---|---|
| Compound of Example 1 | 1.000 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A biaromatic compound having the structural formula (I):

in which:

$R_1$ is an alkyl radical having from 1 to 12 carbon atoms;

$R_2$:

wherein $R_8$ is as defined below;

$R_3$ is a hydrogen atom, a halogen atom, an alkyl radical having from 1 to 12 carbon atoms, a hydroxyl radical, an alkoxy radical having from 1 to 7 carbon atoms, an aralkoxy radical, an aryloxy radical, a polyether radical, a nitro radical, or an amino radical optionally substituted with one or more alkyl radicals having from 1 to 12 carbon atoms, an aryl radical, an aralkyl radical, a heteroaryl radical or a heterocyclic radical;

$R_4$ is an alkyl radical having from 1 to 12 carbon atoms, an aryl radical, an aralkyl radical, a heteroaryl radical, a heterocyclic radical or a 9-fluorenylmethyl radical, a radical —$(CH_2)_a$—$(N-R_{12})_b$—$(CNR_{15})_c$—$R_6$, wherein $R_6$, $R_{12}$, $R_{15}$, a, b and c are as defined below;

$R_6$ is a hydrogen atom, an alkyl radical having from 1 to 12 carbon atoms, an aryl radical, an aralkyl radical, a heteroaryl radical or a heterocyclic radical;

$R_{15}$ is a hydrogen atom, an alkyl radical having from 1 to 2 carbon atoms, an aryl radical, an aralkyl radical, a heteroaryl radical or a heterocyclic radical;

$R_8$ is a radical O—$(CH_2)_v$—$R_9$, an aralkoxy radical, an aryloxy radical, an aryl radical, an aralkyl radical, a heteroaryl radical, a heterocyclic radical, or the radical:

wherein $R_9$, R' and R" are as defined below;

R' is a heteroaryl radical or a heterocyclic radical;

R" is a hydrogen atom, an alkyl radical having from 1 to 12 carbon atoms, an aryl radical, an aralkyl radical, optionally substituted with one or more halogen atoms, a heteroaryl radical, a heterocyclic radical or a radical $(CH_2)_v$—$R_9$, wherein $R_9$ and v are as defined below;

$R_9$ is an aryl, aralkyl or heteroaryl radical, a heterocyclic radical, a radical NH—CO—$R_{10}$, a radical NH—CO—O—$R_{10}$ or C—$R_{10}R_{11}$ or a radical N—$R_{10}$—$R_{11}$, wherein $R_{10}$ and $R_{11}$ are as defined below;

v has the values 1, 2 or 3;

$R_{10}$ is a hydrogen atom, an alkyl radical having from 1 to 12 carbon atoms, an aryl radical, an aralkyl radical, a heteroaryl radical or a heterocyclic radical;

$R_{11}$ is a hydrogen atom or an alkyl radical having from 1 to 3 carbon atoms;

$R_{14}$ is a halogen atom;

A is a radical having the following structure: —$(CH_2)_z$—$(N-R_{12})_y$—$(CO)_x$—$(D)_w$ or —$(CH_2)_z$—$(N-R_{12})_y$—$(CS)_x$—$(D)_w$, wherein D, w, x, y, z and $R_{12}$ are as defined below;

D is an oxygen or sulfur atom, a radical —$NR_{13}$ or a $CH_2$ radical; $R_{13}$ is as defined below; w, x, y and z, which may be identical or difference, have the values 0 or 1, with the proviso that the sum x+y+z+w is greater than 2, and when x=0, then y or w=0;

$R_{12}$ and $R_{13}$ are each a hydrogen atom or an alkyl radical having from 1 to 12 carbon atoms, and the optical and geometrical isomers and salts and mixtures thereof.

2. An alkali metal or alkaline-earth metal, zinc or organic amine salt of the biaromatic compound as defined by claim 1.

3. The biaromatic compound as defined by claim 1, wherein the alkyl radical having from 1 to 3 carbon atoms represented by $R_{11}$ is selected from the group consisting of methyl, ethyl and propyl radicals.

4. The biaromatic compound as defined by claim 1, wherein the alkyl radical having from 1 to 12 carbon atoms represented by $R_1$, $R_3$, $R_4$, $R_6$, $R_{10}$, $R_{12}$, $R_{13}$ or R" is selected from the group consisting of methyl, ethyl, isopropyl, butyl, tert-butyl, hexyl, heptyl, octyl, decyl and cyclohexyl radicals.

5. The biaromatic compound as defined by claim 1, wherein the polyether radical represented by $R_3$ is selected from the group consisting of methoxymethoxy, ethoxymethoxy and methoxyethoxymethoxy radicals.

6. The biaromatic compound as defined by claim 1, wherein the alkoxy radical having from 1 to 7 carbon atoms represented by $R_3$ is selected from the group consisting of methoxy, ethoxy, isopropyloxy, tert-butoxy, hexyloxy, benzyloxy and phenoxy radicals, which may optionally be substituted with an alkyl radical having from 1 to 12 carbon atoms.

7. The biaromatic compound as defined by claim 1, wherein the aryl radical represented by $R_3$, $R_4$, $R_6$, $R_8$, $R_9$, $R_{10}$, $R_{15}$ or R" is selected from the group consisting of phenyl, biphenyl, cinnamyl and naphthyl radicals, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

8. The biaromatic compound as defined by claim 1, wherein the aralkyl radical represented by $R_3$, $R_4$, $R_6$, $R_8$, $R_9$, $R_{10}$, $R_{15}$ or R" is selected from the group consisting of benzyl, phenethyl and 2-naphthylmethyl radicals, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

9. The biaromatic compound as defined by claim 1, wherein the heteroaryl radical represented by $R_3$, $R_4$, $R_6$, $R_8$, $R_9$, $R_{10}$, $R_{15}$, R' or R" is selected from the group consisting of pyridyl, furyl, thienyl, isoxazolyl, oxadiazolyl, oxazolyl, benzimidazolyl, indolyl and benzofuran radicals, optionally substituted with at least one halogen, an alkyl radical having from 1 to 12 carbon atoms, an alkoxy radical having from 1 to 7 carbon atoms, an aralkoxy radical or an aryloxy radical, an aryl radical, a nitro function, a polyether radical, an aryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

10. The biaromatic compound as defined by claim 1, wherein the heterocyclic radical represented by $R_3$, $R_4$, $R_6$, $R_8$, $R_9$, $R_{10}$, $R_{15}$, R' or R" is selected from the group consisting of morpholino, piperidino, piperazino, 2-oxo-1-piperidyl and 2-oxo-1-pyrrolidinyl radicals, optionally substituted with at least one alkyl radical having from 1 to 12 carbon atoms, an alkoxy radical having from 1 to 7 carbon atoms, an aralkoxy radical or an aryloxy radical, an aryl radical, a nitro function, a polyether radical, an aryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

11. The biaromatic compound as defined by claim 1, selected from the group consisting of:

a. 1-[4'-(2-ethoxy-3-morpholin-4-yl-3-oxopropyl)biphenyl-3-yl]-3-heptyl-1-methylurea;

b. 1-{4'-[2-ethoxy-3-(4-methylpiperid-1-yl)-3-oxopropyl]biphenyl-3-yl}-3-heptyl-1-methylurea;

c. 3-benzo[1,2,5]thiadiazol-4-yl-1-{4'-[2-ethoxy-3-(4-methylpiperid-1-yl)-3-oxopropyl]biphenyl-3-yl}-1-methylurea;

d. 1-{4'-[2-ethoxy-3-(4-methylpiperid-1-yl)-3-oxopropyl]biphenyl-3-yl}-1-methyl-3-thiophen-2-ylurea;

e. 2-butoxy-3-[3'-(3-heptyl-1-methylureido)biphenyl-4-yl]propionic acid;

f. 1-{4'-[2-ethoxy-3-(4-methylpiperid-1-yl)-3-oxopropyl]biphenyl-3-yl}-1-methyl-3-(5-methyl-3-phenylisoxazol-4-yl)urea;

g. 2-benzoimidazol-1-yl-N-{4'-[2-ethoxy-3-(4-methylpiperid-1-yl)-3-oxopropyl]biphenyl-3-ylmethyl}-N-methylacetamide;

h. N-{4'-[2-ethoxy-3-(4-methylpiperid-1-yl)-3-oxopropyl]biphenyl-3-ylmethyl}-N-methyl-2-pyrid-4-ylthiazole-4-carboxylamide;

i. N-{4'-[2-ethoxy-3-(4-methylpiperid-1-yl)-3-oxopropyl]biphenyl-3-ylmethyl}-N-methyl-2-pyrid-4-ylthiazole-4-carboxylamide;

j. N-{4'-[2-ethoxy-3-(4-methylpiperid-1-yl)-3-oxopropyl]biphenyl-3-ylmethyl}-N-methyl-6-hydroxynaphthalene-2-carboxylamide;

k. N-[4'-(2-ethoxy-3-morpholin-4-yl-3-oxopropyl)biphenyl-3-ylmethyl]-N-methyl-6-hydroxynaphthalene-2-carboxylamide;

l. N-[4'-(2-ethoxy-3-morpholin-4-yl-3-oxopropyl)biphenyl-3-ylmethyl]-N-methylquinoxaline-6-carboxylamide;

m. N-[4'-(2-ethoxy-3-oxo-3-piperid-1-ylpropyl)biphenyl-3-ylmethyl]-N-methyl-6-(2-methoxyethoxymethoxy)naphthalene-2-carboxylamide;

n. N-{4'-[2-ethoxy-3-(4-methylpiperid-1-yl)-3-oxopropyl]biphenyl-3-ylmethyl}-N-methyl-6-(2-methoxyethoxymethoxy)naphthalene-2-carboxylamide;

o. N-{4'-[2-ethoxy-3-oxo-3-(4-phenylpiperid-1-yl)propyl]biphenyl-3-ylmethyl}-N-methyl-6-(2-methoxyethoxymethoxy)naphthalene-2-carboxylamide;

p. N-{4'-[2-ethoxy-2-(3-methylbutylcarbamoyl)ethyl]biphenyl-3-ylmethyl}-N-methyl-6-(2-methoxyethoxymethoxy)naphthalene-2-carboxylamide;

q. N-{4'-[2-(cyclohexylmethylcarbamoyl)-2-ethoxyethyl]biphenyl-3-ylmethyl}-N-methyl-6-(2-methoxyethoxymethoxy)naphthalene-2-carboxylamide;

r. N-{4'-[2-ethoxy-2-(ethylpyrid-4-ylmethylcarbamoyl) ethyl]biphenyl-3-ylmethyl}-N-methyl-6-(2-methoxy-ethoxymethoxy)naphthalene-2-carboxylamide;
s. N-(4'-{2-[(2-dimethylaminoethyl)ethylcarbamoyl]-2-ethoxyethyl}biphenyl-3-ylmethyl)-N-methyl-6-(2-methoxyethoxymethoxy)naphthalene-2-carboxylamide;
t. N-{4'-[2-ethoxy-2-(2-piperid-1-ylethylcarbamoyl) ethyl]biphenyl-3-ylmethyl}-N-methyl-6-(2-methoxy-ethoxymethoxy)naphthalene-2-carboxylamide;
u. N-[4'-(2-ethoxy-3-morpholin-4-yl-3-oxopropyl)biphenyl-3-ylmethyl]-N-methyl-6-(2-methoxy-ethoxymethoxy)naphthalene-2-carboxylamide;
v. N-{4'-[2-(benzylmethylcarbamoyl)-2-ethoxyethyl]biphenyl-3-ylmethyl}-N-methyl-6-(2-methoxy-ethoxymethoxy)naphthalene-2-carboxylamide;
w. N-{4'-[2-ethoxy-3-(4-methylpiperazin-1-yl)-3-oxopropyl]biphenyl-3-ylmethyl}-N-methyl-6-(2-methoxy-ethoxymethoxy)naphthalene-2-carboxylamide;
x. N-{4'-[2-(cyclohexylmethylcarbamoyl)-2-ethoxyethyl]biphenyl-3-ylmethyl}-N-methyl-6-(2-methoxy-ethoxymethoxy)naphthalene-2-carboxylamide;
y. 1-{4'-[2-cyclopropylmethoxy-3-(4-methylpiperid-1-yl)-3-oxopropyl]biphenyl-3-yl}-3-hexyl-1-methylthiourea;
z. 1-{4'-[2-ethoxy-3-(4-methylpiperid-1-yl)-3-oxopropyl] biphenyl-3-yl}-3-hexyl-1-methylthiourea;
aa. 1-[4'-(2-ethoxy-3-morpholin-4-yl-3-oxopropyl)biphenyl-3-yl]-3-hexyl-1-methylthiourea;
ab. [4'-(2-ethoxy-3-morpholin-4-yl-3-oxopropyl)-4-fluorobiphenyl-3-ylmethyl]methyloctanoylamide;
ac. 4'-(2-ethoxy-3-morpholin-4-yl-3-oxopropyl)-6-fluorobiphenyl-3-ylmethyl]methyloctanoylamide;
ad. 1-[4'-(2-ethoxy-3-morpholin-4-yl-3-oxopropyl)-6-fluorobiphenyl-3-yl]-3-heptyl-1-methylurea;
ae. 1-{4'-[2-ethoxy-3-(4-methylpiperid-1-yl)-3-oxopropyl]-6-fluorobiphenyl-3-yl}-3-heptyl-1-methylurea;
af. 1-{4'-[2-ethoxy-3-(4-methylpiperid-1-yl)-3-oxopropyl]-4-fluorobiphenyl-3-yl}-3-heptyl-1-methylurea;
ag. 1-{4'-[2-ethoxy-3-(4-methylpiperid-1-yl)-3-oxopropyl]-3'-fluorobiphenyl-3-yl}-3-heptyl-1-methylurea;
ah. 5-oxo-N-{4'-[2-ethoxy-3-(4-methylpiperid-1-yl)-3-oxopropyl]biphenyl-3-ylmethyl}-N-methylhexanoylamide;
ai. {4'-[2-ethoxy-3-(4-methylpiperid-1-yl)-3-oxopropyl] biphenyl-3-ylmethyl}methylhexanoylamide;
aj. 4-acetylamino-N-{4'-[2-ethoxy-3-(4-methylpiperid-1-yl)-3-oxopropyl]biphenyl-3-ylmethyl}-N-methylbutyramide;
ak. N-{4'-[2-cyclopropylmethoxy-3-(4-methylpiperid-1-yl)-3-oxopropyl]biphenyl-3-ylmethyl}-N-methyloctanoylamide;
al. N-[4'-(2-cyclopropylmethoxy-3-morpholin-4-yl-3-oxopropyl)biphenyl-3-ylmethyl]-N-methyloctanoylamide;
am. N-[4'-(2-ethoxy-3-morpholin-4-yl-3-oxopropyl)biphenyl-3-ylmethyl]-N-methyloctanoylamide;
an. N-{4'-[2-ethoxy-3-(4-methylpiperid-1-yl)-3-oxopropyl]biphenyl-3-ylmethyl}-N-methyloctanoylamide;
ao. N-[4'-(2-ethoxy-3-oxo-3-piperid-1-ylpropyl)biphenyl-3-ylmethyl]-N-methyloctanoylamide;
ap. 1-[4'-(2-ethoxy-3-oxo-3-piperid-1-ylpropyl)biphenyl-3-yl]-3-heptyl-1-methylurea;
aq. 1-[4'-(2-cyclopropylmethoxy-3-morpholin-4-yl-3-oxopropyl)biphenyl-3-yl]-3-heptyl-1-methylurea;
ar. 1-[4'-(2-cyclopropylmethoxy-3-morpholin-4-yl-3-oxopropyl)biphenyl-3-yl]-1-methyl-3-pentylurea;
as. 1-[4'-(2-cyclopropylmethoxy-3-oxo-3-piperid-1-ylpropyl)biphenyl-3-yl]-1-methyl-3-pentylurea;
at. 1-[4'-(2-cyclopropylmethoxy-3-oxo-3-piperid-1-ylpropyl)biphenyl-3-yl]-3-heptyl-1-methylurea;
au. 1-{4'-[2-cyclopropylmethoxy-3-(4-methylpiperid-1-yl)-3-oxopropyl]biphenyl-3-yl}-3-heptyl-1-methylurea;
av. 3-heptyl-1-methyl-1-{4'-[3-(4-methylpiperid-1-yl)-3-oxo-2-propoxypropyl]biphenyl-3-yl}urea;
aw. 1-methyl-1-[4'-(3-oxo-3-piperid-1-yl-2-propoxypropyl)biphenyl-3-yl]-3-pentylurea; and
ax. 3-heptyl-1-methyl-1-[4'-(3-oxo-3-piperid-1-yl-2-propoxypropyl)biphenyl-3-yl]urea; and mixtures thereof.

12. The biaromatic compound as defined by claim 1, having at least one of the following characteristics:

$R_8$ is a radical NR'R";

A is the linking radical of structure —CH$_2$N(R$_{12}$)—CO or N(R$_{12}$)—CO—(D)$_w$ in which w=0 or 1; and/or $R_4$ is an alkyl, aryl or heteroaryl radical.

13. A pharmaceutical composition comprising a thus effective amount of the biaromatic compound as defined by claim 1, formulated into a physiologically acceptable support therefor.

14. A cosmetic composition comprising a thus effective amount of the biaromatic compound as defined by claim 1, formulated into a cosmetically acceptable support therefor.

* * * * *